(12) United States Patent
Moore

(10) Patent No.: US 11,753,428 B2
(45) Date of Patent: Sep. 12, 2023

(54) BINUCLEAR IRON-FUSED PORPHYRIN

(71) Applicant: Gary F. Moore, Mesa, AZ (US)

(72) Inventor: Gary F. Moore, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/944,783

(22) Filed: Sep. 14, 2022

(65) Prior Publication Data

US 2023/0088889 A1 Mar. 23, 2023

Related U.S. Application Data

(60) Provisional application No. 63/244,682, filed on Sep. 15, 2021.

(51) Int. Cl.
 *C07F 15/02* (2006.01)
 *C07F 15/03* (2006.01)

(52) U.S. Cl.
 CPC ........... *C07F 15/025* (2013.01); *C07F 15/03* (2013.01)

(58) Field of Classification Search
 CPC .............................. C07F 15/025; C07F 15/03
 See application file for complete search history.

(56) References Cited

FOREIGN PATENT DOCUMENTS

JP  2001-089490  4/2001
JP  2005-276510  10/2005

OTHER PUBLICATIONS

Brennan et al. "Selective oxidative synthesis of meso-beta fused porphyrin dimers", Journal of Porphyrins and Phthalocyanines, vol. 17, No. 04, pp. 247-251 (2013).*
Alben et al., "Infrared Spectroscopy of Poryphyrins," Ann. N. Y. Acad. Sci., 1973, 206, 278-295.
Artero et al., "Toward the rational benchmarking of homogeneous H2-evolving catalysts," Energy Environ. Sci., 2014, 7, 3808-3814.
Azcarate et al., "Through-Space Charge Interaction Substituent Effects in Molecular Catalysis Leading to the Design of the Most Efficient Catalyst of CO2-to-CO Electrochemical Conversion," J. Am. Chem. Soc., 2016, 138, 16639-16644.
Bard et al., Electrochemical methods: fundamentals and applications, 2nd Ed., Wiley & Sons, 2001; p. 293.
Bar-Ilan et al., "Heterogeneous and Homogeneous Catalysis by Substituted Cobalt Tetraphenylporphyrins, and Correlations with IR Spectra," J. Catal., 1974, 33, 68-73.
Beiler et al., "Cobalt Porphyrin—Polypyridyl Surface Coatings for Photoelectrosynthetic Hydrogen Production," Inorg. Chem., 2017, 56, 12178-12185.
Beyene et al., "Recent progress on metalloporphyrin-based hydrogen evolution catalysis," Coord. Chem. Rev., 2020, 410, 213234, 25 pages.
Bhugun et al., "Catalysis of the Electrochemical Reduction of Carbon Dioxide by Iron(0) Porphyrins. Synergistic Effect of Lewis Acid Cations," J. Phys. Chem., 1996, 100, 19981-19985.
Bhugun et al., "Catalysis of the Electrochemical Reduction of Carbon Dioxide by Iron(0) Porphyrins: Synergy Stic Effect of Weak Bronsted Acids," J. Am. Chem. Soc., 1996, 118, 1769-1776.
Bhugun et al., "Homogeneous Catalysis of Electrochemical Hydrogen Evolution by Iron(0) Porphyrins," J. Am. Chem. Soc., 1996, 118, 3982-3983.
Bhugun et al., "Ultraefficient Selective Homogeneous Catalysis of the Electrochemical Reduction of Carbon Dioxide by an Iron(0) Porphyrin Associated with a Weak Bronsted Acid Cocatalyst," J. Am. Chem. Soc., 1994, 116, 5015-5016.
Boucher et al., "The Infared Spectra of Metalloporphyrins (4000-160 Cm 1)1," J. Am. Chem. Soc. 1967, 89, 1340-1345.
Brennan et al., "Oxidative coupling of porphyrins using copper(II) salts," Chem. Common., 2011, 47, 10034-10036.
Briois et al., "SAMBA.: The 4-40 keV X-ray absorption spectroscopy beamline at. SQLEIL," UVX2010, 2011, p. 41-47.
Cheng et al., "Triply Fused ZnII-Porphyrin Oligomers: Synthesis, Properties, and Supramolecular Interactions with Single-Walled Carbon Nanotubes (SWNTs)," Chem. Eur. J., 2006, 12, 6062-6070.
Cho et al., "Photophysical Properties of Porphyrin Tapes," J. Am. Chem. Soc., 2002, 124, 14642-14654.
Connelly et al., "Chemical Redox Agents for Organometallic Chemistry," Chem. Rev., 1996, 96 (2), 877-910.
Costentin et al., "A Local Proton Source Enhances CO2 Electroreduction to CO by a Molecular Fe Catalyst," Science, 2012, 338, 90-94.
Costentin et al., "A Pioneering Career in Electrochemistry: Jean-Michel Savéant," ACS Catal., 2021, 11, 3224-3238.
Costentin et al., "Efficient and selective molecular catalyst for the CO2-to-CO electrochemical conversion in water," Proc. Nat. Acad. Sci., 2015, 112, 6882-6886.
Costentin et al., "Heterogeneous Molecular Catalysis of Electrochemical Reactions: Volcano Plots and Catalytic Tafel Plots," ACS Appl. Mater. Interfaces, 2017, 9, 19894-19899.
Costentin et al., "Molecular Catalysis of H2 Evolution: Diagnosing Heterolytic versus Homolytic Pathways," J. Am. Chem. Soc., 2014, 136, 13727-13734.
Costentin et al., "Pendant Acid-Base Groups in Molecular Catalysts: H-Bond Promoters or Proton Relays? Mechanisms of the Conversion of CO2 to CO by Electrogenerated Iron(0)Porphyrins Bearing Prepositioned Phenol Functionalities," J. Am. Chem. Soc., 2014, 136, 11821-11829.
Costentin et al., "Proton-Coupled Electron Transfer Cleavage of Heavy-Atom Bonds in Electrocatalytic Processes. Cleavage of a C—O Bond in the Catalyzed Electrochemical Reduction of CO2," J. Am. Chem. Soc., 2013, 135, 9023-9031.

(Continued)

Primary Examiner — Joseph R Kosack
(74) Attorney, Agent, or Firm — Fish & Richardson P.C.

(57) ABSTRACT

A binuclear Fe(III) fused porphyrin. Synthesizing the binuclear fused porphyrin includes combining free-base fused-porphyrin and a solvent to yield a solution, refluxing the solution, combining a metal salt with the solution, and removing the solvent from the solution.

10 Claims, 6 Drawing Sheets

(56) References Cited

OTHER PUBLICATIONS

Costentin et al., "Turnover Numbers Turnover Frequencies, and Overpotential in Molecular Catalysis of Electrochemical Reactions. Cyclic Voltammetry and Preparative-Scale Electrolysis," J. Am. Chem. Soc., 2012, 134, 11235-11242.

Costentin et al., "Ultraefficient homogeneous catalyst for the CO2-to-CO electrochemical conversion," Proc. Nat. Acad. Sci., 2014, 111, 14990-14994.

Cruz et al., "Six-Electron Chemistry of a Binuclear Fe(III) Fused Porphyrin," ChemElectroChem, 2021, 8(19):3614-3620.

Diev et al., "Fused Pyrene-Diporphyrins: Shifting Near-Infrared Absorption to 1.5 um and Beyond," Angew. Chem. Int. Ed., 2010, 49, 5523-5526.

Dimé et al., "Versatile redox reactivity of triaryl-meso-substituted Ni(II) porphyrin," Dalton Trans., 2014, 43, 14554-14564.

Fendt et al., "meso,meso-Linked and Triply Fused Diporphyrins with Mixed-Metal Ions: Synthesis and Electrochemical Investigations," Eur. J. Org. Chem., 2007, 2007, 4659-4673.

Feng et al., "Switchable regioselectivity in the PIFA—BF3 Et2O mediated oxidative coupling of meso-brominated Ni(II) porphyrin," Org. Biomol. Chem., 2014, 12, 6990-6993.

Feng et al., "Synthesis of directly fused porphyrin dimers through Fe(OTf)3-mediated oxidative coupling," Org. Biomol. Chem., 2015, 13, 2566-2569.

Gotico et al., "Recent advances in metalloporphyrin-based catalyst design towards carbon dioxide reduction: from bio-inspired second coordination sphere modifications to hierarchical architectures," Dalton Trans., 2020, 49, 2381-2396.

Hammouche et al., "Chemical Catalysis of Electrochemical Reactions. Homogeneous Catalysis of the Electrochemical Reduction of Carbon Dioxide by Iron("0") Porphyrins. Role of the Addition of Magnesium Cations," J. Am. Chem. Soc., 1991, 113, 8455-8466.

Heo et al., "Molecular-Shape-Dependent Photophysical Properties of meso-β Doubly Linked Zn(II) Porphyrin Arrays and Their Indene-Fused Analogues," J. Phys. Chem. B, 2010, 114, 14528-14536.

Huerta-Flores et al., "Fused Porphyrin Thin Films as Heterogeneous Visible-Light Active Photocatalysts with Well-Defined Active Metal Sites for Hydrogen Generation," ACS Appl, Mater, Interfaces, 2020, 3, 9848-9855.

Ikeda et al., "Meso-β Doubly Linked Zn(II) Porphyrin Trimers: Distinct, anti-versus-syn Effects on Their Photophysical Properties," Org. Lett., 2009, 11, 3080-3083.

Ikeue et al., "The Importance of β-β Bond for Long-Range /Antiferromagnetic Coupling in Directly Linked Copper(II) and Silver(II) Diporphyrins," Angew. Chem. Int. Ed., 2005, 44, 6899-6901.

Kadish et al., "Electrochemistry/ of porphyrins and related macrocycles," J. Solid State Electrochem., 2003, 7, 254-258.

Kamo et al., "Metal-Dependent Regioselective Oxidative Coupling of 5,10,15-Triarylporphyrins with DDQ-Sc(OTf)3 and Formation of an Oxo-quinoidal Porphyrin," Org, Lett., 2003, 5, 2079-2082.

Khusnutdinova et al., "Electrocatalytic Properties of Binuclear Cu(II) Fused Porphyrins for Hydrogen Evolution," ACS Catal., 2018, 8, 9888-9898.

Khusnutdinova et al., "Metalloporphyrin-modified semiconductors for solar fuel production," Chem. Sci., 2017, 8, 253-259.

Khusnutdinova et al., "Vibrational structure analysis of cobalt fluoro-porphyrin surface coatings on gallium phosphide," J. Porphyrins Phthalocyanines, 2018, 22, 461-468.

Khusnutdinova et al., "Synthesis and characterization of a cobalt(II) tetrakis(3-fluorophenyl) porphyrin with a built-in 4-vinylphenyl surface attachment moiety," Photosynthetica, 2018, 56, 67-74.

Kirn et al., "Photophysical Properties of Directly Linked Linear Porphyrin Arrays," J. Phys. Chem. A, 2003, 107, 8791-8816.

Kim et al., "Large Two-Photon Absorption (TPA) Cross-Section of Directly Linked Fused Diporphyrins," J. Phys. Chem. A, 2005, 109, 2996-2999.

Kincaid et al., "Vibrational Spectra of Transition Metal Compleses of Tetraphenylporphine," J. Inorg, Nucl. Chem. 1975, 37, 85-89.

Lee et al., "Stable Singlet Biradicals of Rare-Earth-Fused Diporphyrin-Triple-Decker Complexes with Low Energy Gaps and Multi-Redox States," Chem. Eur. J., 2019, 25, 3240-3243.

Lexa et al., "Electroreductive Alkylation of Iron in Porphyrin Complexes. Electrochemical and Spectral Characteristics of σ-Alkyliron Porphyrins," J. Am. Chem. Soc., 1981, 103, 6806-6812.

Lexa et al., "Molecular Environment Effects in Redox Chemistry. Electrochemistry of Ether-Linked Basket-Handle and Amide-Linked Basket-Handle and Picket-Fence Iron Porphyrins," J. Am. Chem. Soc., 1984, 106, 4755-4765.

Lexa et al., "Electroreductive Alkylation of Iron Porphyrins. Iron(III), Iron(II), and Iron(I) Alkyl Complexes from the Reaction of Doubly Reduced Iron(II) Porphyrins with Alkyl Halides," Organometallics, 1986, 5, 1428-1434.

Liu et al., "The Diversity of Electron-Transport Behaviors of Molecular Junctions: Correlation with the Electron-Transport Pathway," ChemPhysChem, 2010, 11, 1895-1902.

Luca et al., "Redox-active ligands in catalysis," Chem. Soc. Rev., 2013, 42, 1440-1459.

Lyaskovskyy et al., "Redox Non-Innocent Ligands: Versatile New Tools to Control Catalytic Reactions," ACS Catal., 2012, 2, 270-279.

Lysenko et al., "Diverse porphyrin dimers as candidates for high-density charge-storage molecules," J. Porphyrins Phthalocyanines, 2006, 10, 22-32.

Mai et al., "Synthesis and characterization of diporphyrin sensitizers for dye-sensitized solar cells," Chem. Commun., 2010, 46, 809-811.

Mashiko et al., "Nature of Iron(I) and Iron(0) Tetraphenylporphyrin Complexes. Synthesis and Molecular Structure of (Dibenzo-18-crown-6)bis(tetrahydrofuran)sodium (meso-Tetraphenylporphinato)ferrate and Bis[tris(tetrahydrofuran)sodium] (meso-Tetraphenylporphinato) ferrate," Inorg. Chem., 1984, 23, 3192-3196.

Muranaka et al., "Magnetic Circular Dichroism Study of Directly Fused Porphyrins," ChemPhysChem, 2005, 6, 171-179.

Nakamura et al., "Oxidative direct coupling of metalloporphyrins," J. Porphyrins Phthalocyanines, 2003, 7, 264-269.

Nalin De Silva, "Meso-β doubly linked and meso-meso, β-β, β-β triply linked oligoporphyrin molecular tapes as potential non linear optical (NLO) materials: quantum chemical calculations," J. Mol. Struct., 2005, 726, 39-45.

Newville, "EXAFS analysis using FEFF and FEFFIT," J. Synchrotron Radiat., 2001, 8 (2), 96-100.

Ouyang et. ah, "An Efficient PIFA-Mediated Synthesis of Fused Diporphyrin and Triply-Singly Interlacedly Linked Porphyrin Array," Org. Lett., 2009, 11, 5266-5269.

Römelt et al., "Electronic Structure of a Formal Iron(0) Porphyrin Complex Relevant to CO2 Reduction," Inorg. Chem., 2017, 56, 4745-4750.

Sahoo et al., "Synthesis of Brominated Directly Fusted Diporphyrins through Gold(III)-Mediated Oxidation," Org. Lett., 2006, 8, 4141-4144.

Sugiura et al., "Synthesis of the porphyrin-fused porphyrin, [2]porphyracene," Chem. Commun., 1999, p. 1957-1958.

Sun et al., "Slow Electron Transfer Rates for Fluorinated Cobalt Porphyrins: Electronic and Conformational Factors Modulating Metalloporphyrin ET," Inorg. Chem., 2003, 42, 6032-6040.

Tanaka et al., "Synthesis and Properties of Hybrid Porphyrin Tapes," Chem. Eur. J., 2011, 17, 14400-14412.

Tanaka et al., "Conjugated porphyrin arrays: synthesis, properties and applications for functional materials," Chem. Soc. Rev., 2015, 44, 943-969.

Trasatti, "The Absolute Electrode Potential: An Explanatory Note," J. Electroanal. Chem., 1986, 209, 417-428.

Tsuda et al., "Discrete Conjugated Porphyrin Tapes with an Exceptionally Small Bandgap," Adv. Mater., 2002, 14, 75-79.

Tsuda et al., "Completely Fused Diporphyrins and Tri porphyrin," Angew. Chem. Int. Ed. 2000, 39, 2549-2552.

Tsuda et al., "Doubly meso-β-Linked Diporphyrins from Oxidation of 5,10,15-Triaryl-Substituted NiII- and PdII-Porphyrins," Angew. Chem. Int. Ed. 2000, 39, 558-561.

(56) References Cited

OTHER PUBLICATIONS

Tsuda et al., "Synthesis of meso-β doubly linked porphyrin tapes," Chem. Commun., 2003, 3, 1096-1097.

Tsuda et al., "Syntheses, Structural Characterizations, and Optical and Electrochemical Properties of Directly Fused Diporphyrins," J. Am. Chem. Soc., 2001, 123, 10304-10321.

Tsuda et al., "Fully Conjugated Porphyrin Tapes with Electronic Absorption Bands That Reach into Infrared," Science, 2001, 293, 79-82.

Wadsworth et al., "Expanding the Redox Range of Surface-Immobilized Metallocomplexes Using Molecular Interfaces," ACS Appl. Mater. Interfaces, 2020, 12, 3903-3911.

Westre et al., "A Multiplet Analysis of Fe K-Edge 1s 3d Pre-Edge Features of Iron Complexes," J. Am. Chem. Soc., 1997, 119, 6297-6314.

Wu et al., "Electroreduction of CO2 Catalyzed by a Heterogenized Zn-Porphyrin Complex with a Redox-Innocent Metal Center," ACS Cent. Sci., 2017, 3, 847-852.

Yoon et al., "Photophysics of meso-β Doubly Linked Ni(II) Porphyrin Arrays: Large Two-Photon Absorption Cross-Section and Fast Energy Relaxation Dynamics," J. Am. Chem. Soc., 2007, 129, 10080-10081.

Zhang et al., "Energy-Related Small Molecule Activation Reactions: Oxygen Reduction and Hydrogen and Oxygen Evolution Reactions Catalyzed by Porphyrin-and Corrole-Based Systems," Chem. Rev., 2017, 117, 3717-3797.

Zhang et al., "A comparative study of one- and two-photon absorption properties of meso-meso singly, meso-β doubly and meso-meso β-β β-β triply linked ZnII-porphyrin oligomers," J. Mol. Struct., 2007, 804, 21-29.

* cited by examiner

[Fe₂FP]Cl₂

[FeTTP]Cl

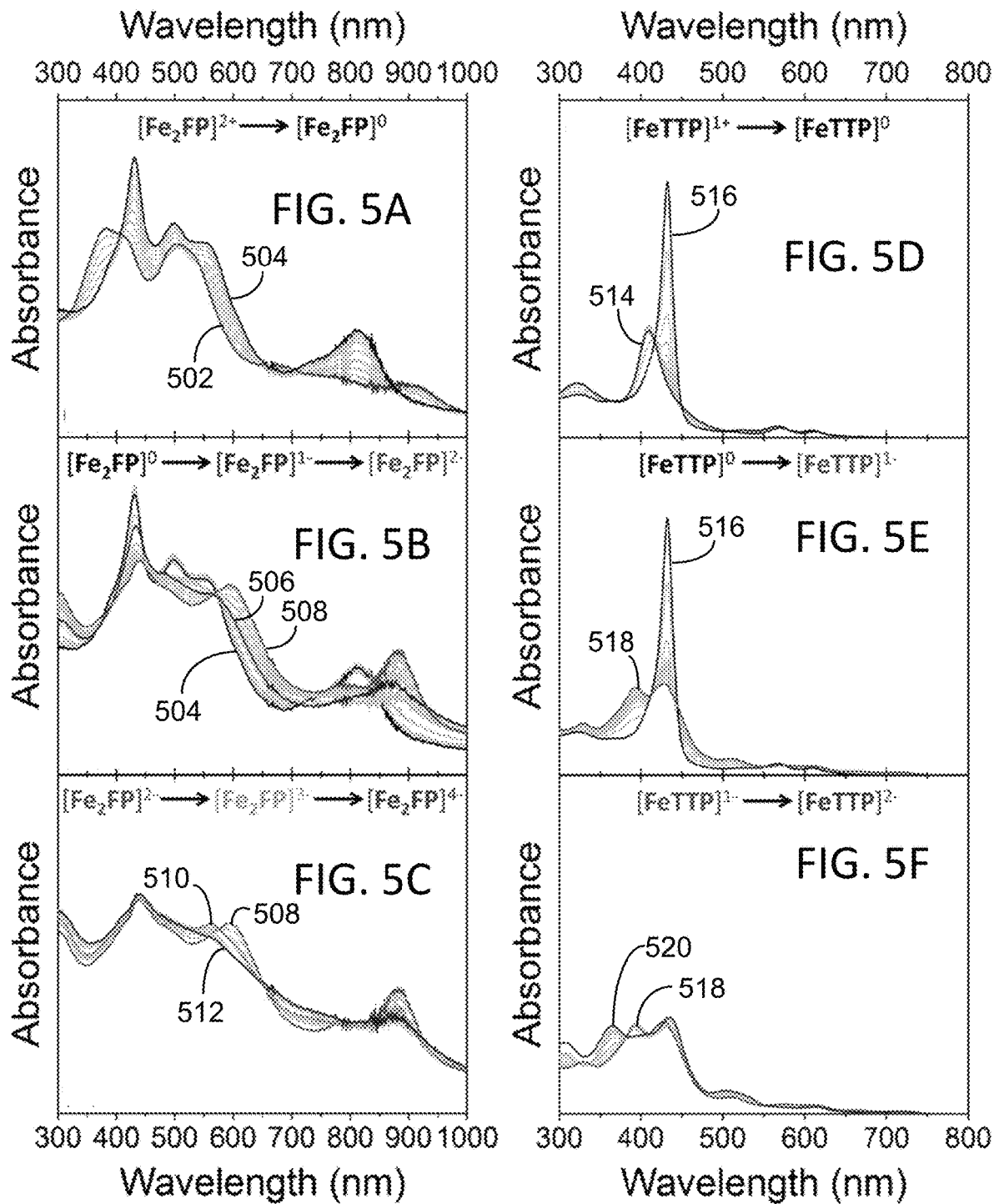

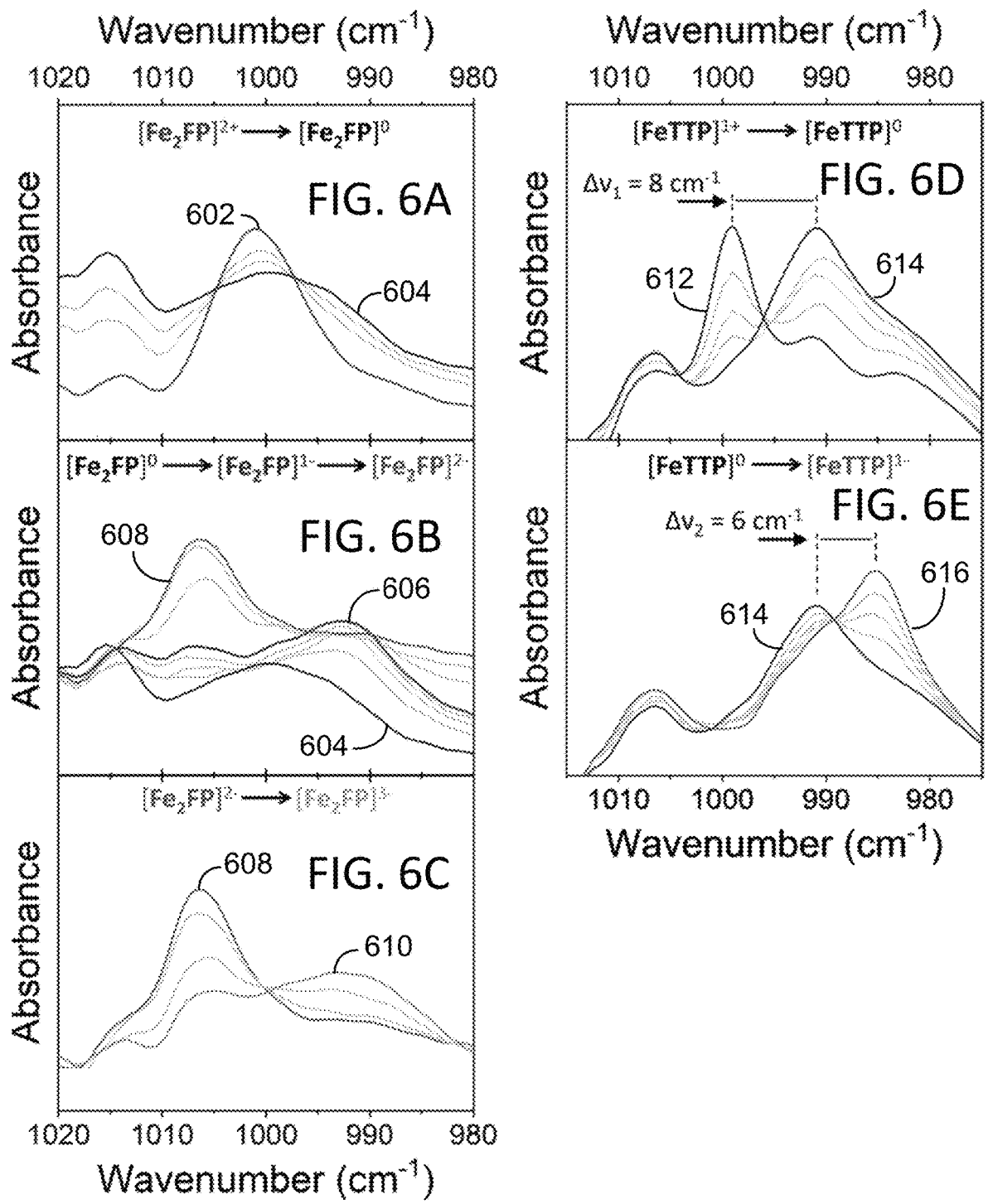

BINUCLEAR IRON-FUSED PORPHYRIN

CROSS-REFERENCE TO RELATED APPLICATION

This application claims the benefit of U.S. Patent Application No. 63/244,682 filed on Sep. 15, 2021, which is incorporated herein by reference in its entirety.

TECHNICAL FIELD

This invention relates to a fused-iron-porphyrin having bimetallic-iron sites, a π-extended ligand capable of delocalizing electrons across the multimetallic scaffold, and the ability to store up to six electrons.

BACKGROUND

Multinuclear fused porphyrins have unique optical properties resulting from their extended aromaticity. They can be used in applications involving non-linear optic materials, molecular wires, and supramolecular chemistry.

SUMMARY

This disclosure describes a binuclear iron-fused porphyrin and methods of synthesizing the porphyrin. Ultraviolet-visible spectroscopy confirms the extended electronic structure of this macrocycle. In addition, Fourier transform infrared spectroscopy indicates the iron centers experience a relatively rigid ligand environment as compared to a structurally related mononuclear complex featuring an 18 π-aromatic porphyrin ligand. X-ray photo-electron and X-ray absorption near edge spectroscopies confirm the iron centers of both assemblies are Fe(III) in the as-prepared, resting state.

A first general aspect includes a binuclear iron-fused porphyrin.

Implementation of the first general aspect can include one or more of the following features.

Certain implementations have the structure:

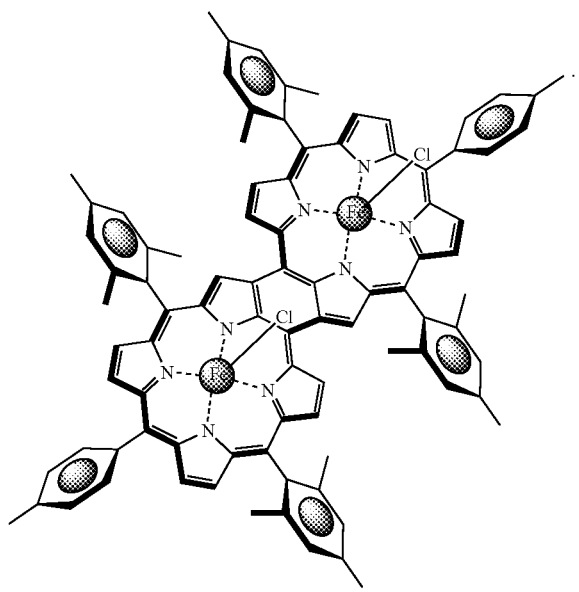

In some cases, the structure includes a π-extended ligand configured to delocalize electrons across the bimetallic iron sites. The structure is configured to store up to six electrons.

In a second general aspect, synthesizing a binuclear fused porphyrin includes combining free-base fused-porphyrin and a solvent to yield a solution, refluxing the solution, combining a metal salt with the solution, and removing the solvent from the solution to yield the binuclear fused porphyrin.

Implementations of the second general aspect can include one or more of the following features.

In some cases, the solvent includes dichloromethane and methanol. In one example, a volume ratio of dichloromethane to methanol can be about 5:1. The metal salt can include $FeCl_2$. In one example, a molar ratio of the metal salt to the free-base fused-porphyrin is about 60:1. Refluxing the solution can occur under an argon atmosphere. Removing the solvent can occur under reduced pressure. In some cases, combining the metal salt with the solution includes combining the metal salt in discrete portions over time. Certain implementations further include purifying the binuclear fused porphyrin. In some implementations, the binuclear fused porphyrin is represented by structure shown with respect to the first general aspect.

In comparison with the mononuclear porphyrin, electrochemical measurements show there is a doubling of the number of redox events associated with the fused, binuclear complex. Features of the fused-iron-porphyrin include: bimetallic-iron sites; a π-extended ligand capable of delocalizing electrons across the multimetallic scaffold; and the ability to store up to six electrons.

The details of one or more embodiments of the subject matter of this disclosure are set forth in the accompanying drawings and the description. Other features, aspects, and advantages of the subject matter will become apparent from the description, the drawings, and the claims.

BRIEF DESCRIPTION OF DRAWINGS

FIGS. 5A-5C show UV-Vis-NIR absorption spectra of $[Fe_2FP]Cl_2$ recorded in a solution polarized at potentials to generate $[Fe_2FP]^{2+}$, $[Fe_2FP]^0$, $[Fe_2FP]^{1-}$, $[Fe_2FP]^{2-}$, $[Fe_2FP]^{3-}$, and $[Fe_2FP]^{4-}$. FIGS. 5D-5F show spectra of [FeTTP]Cl recorded in a solution polarized at potentials to generate $[FeTTP]^{1+}$, $[FeTTP]^0$, $[FeTTP]^{1-}$, and $[FeTTP]^{2-}$.

FIGS. 6A-6C show FTIR absorption spectra of $[Fe_2FP]Cl_2$ recorded in a solution polarized at potentials to generate $[Fe_2FP]^{2+}$, $[Fe_2FP]^0$, $[Fe_2FP]^{1-}$, $[Fe_2FP]^{2-}$, and $[Fe_2FP]^{3-}$.

FIGS. 6D-6E show spectra of [FeTTP]Cl recorded in solution polarized at potentials to generate [FeTTP]$^{1+}$, [FeTTP]$^{0}$, and [FeTTP]$^{1-}$.

DETAILED DESCRIPTION

Figures 1A, 1B:
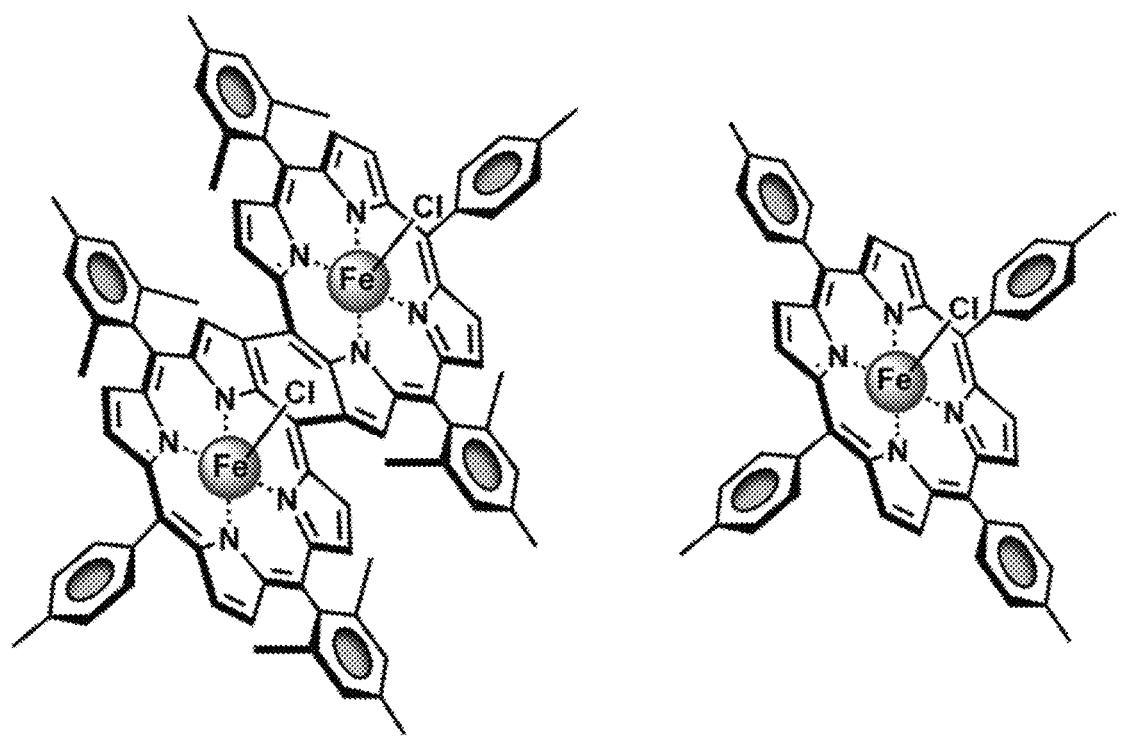
FIGS. 1A and 1B depict molecular structures of binuclear iron-fused porphyrin $[Fe_2FP]Cl_2$ including meso-β doubly-fused 5,24-di-(p-tolyl)-10,19,29,38-tetramesitylporphyrin (free-base fused-porphyrin, FP) and mononuclear iron porphyrin [FeTTP]Cl including 5,10,15,20-tretra-p-tolylporphyrin (TTP), respectively.

This disclosure describes a binuclear iron-fused porphyrin [Fe$_2$FP]Cl$_2$ including meso-β doubly-fused 5,24-di-(p-tolyl)-10,19,29,38-tetramesitylporphyrin (free-base fused-porphyrin, FP) shown in FIG. 1A and methods of synthesizing the porphyrin. Ultraviolet-visible spectroscopy confirms the extended electronic structure of this macrocycle. Fourier transform infrared spectroscopy indicates the Fe centers experience a relatively rigid ligand environment as compared to a structurally related mononuclear complex [FeTTP]Cl featuring an 18 π-aromatic porphyrin ligand 5,10,15,20-tretra-p-tolylporphyrin (TTP) shown in FIG. 1B. X-ray photo-electron and X-ray absorption near edge spectroscopies confirm the iron centers of both assemblies are Fe(III) in the as-prepared, resting state. In comparison with mononuclear porphyrin shown in FIG. 1B, electrochemical measurements show there is a doubling of the number of redox events associated with the fused, binuclear complex [Fe$_2$FP]Cl$_2$. Features of the fused-iron-porphyrin include bimetallic iron sites, a π-extended ligand environment configured to delocalize electrons across the bimetallic iron sites and capable of storing up to six electrons.

EXAMPLES

Synthesis

Figure 2:
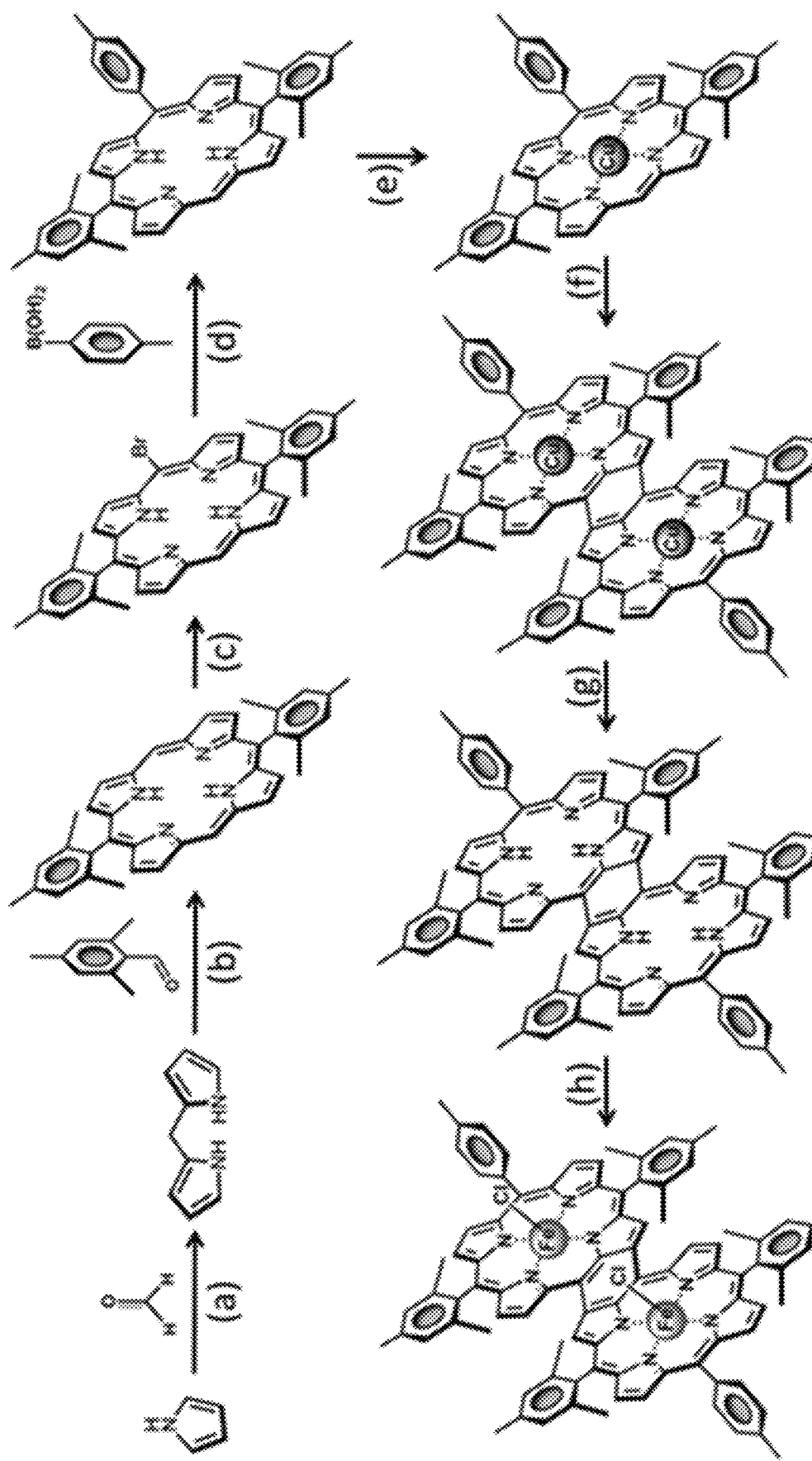
FIG. 2 shows a portion of a synthetic route for preparing $[Fe_2FP]Cl_2$.

Binuclear iron-fused porphyrin [Fe$_2$FP]Cl$_2$ was prepared via an 8-step synthetic route following the scheme depicted in FIG. 2. The identity and purity of 5,10,15,20-tretra-p-tolylporphyrin (TTP), [FeTTP]Cl, and meso-β doubly-fused 5,24-di-(p-tolyl)-10,19,29,38-tetramesitylporphyrin (free-base fused-porphyrin, FP) were confirmed via matrix-assisted laser desorption/ionization time-of-flight mass spectrometry (MALDI-TOF MS), Ultraviolet-visible (UV-Vis) spectroscopy, Fourier transform infrared (FTIR), Nuclear Magnetic Resonance (NMR) spectroscopies, and homogenous electrochemical analysis.

FIG. 2 shows a portion of a synthetic route for preparing [Fe$_2$FP]Cl$_2$. (a) TFA, 50° C., 5 min. (b) 1. BF$_3$·Et$_2$O, CHCl$_3$, rt, 30 min. 2. DDQ, reflux, 1 h. (c) NBS, Pyridine, CHCl$_3$, 0° C., 20 min. (d) p-Tolylboronic acid, K$_3$PO$_4$, Pd(PPh$_3$)$_4$, Tol:H$_2$O:MetOH, reflux, overnight. (e) CuAc$_2$, DCM:MetOH, reflux, overnight. (f) Cu(BF$_4$)$_2$·6H$_2$O, MeNO$_2$, rt, 2 h. (g) TFA:H$_2$SO$_4$, rt, 20 min. (h) FeCl$_2$·4H$_2$O, DCM:MetOH, reflux, overnight. All reactions were performed under Ar atmosphere.

Referring to step (h) in FIG. 2, [Fe$_2$FP]Cl$_2$ was synthesized by adding FeCl$_2$·4H$_2$O (187.8 mg, 945.3 μmol) in approximately three equivalent portions over 30 min to refluxing solution of FP (20 mg, 15.7 μmol) in a 5:1 solution of dichloromethane:methanol. The mixture was refluxed overnight under an argon atmosphere before removing the solvent under reduced pressure. The crude product was purified via column chromatography using alumina as the stationary phase and 50:50:3 dichloromethane:hexane:methanol as the mobile phase. The resulting dark purple fractions were concentrated under reduced pressure before redissolving in dichloromethane and washing with an aqueous 6 M HCl solution using a separatory funnel. Collection of the resulting organic phase and removal of the solvent under reduced pressure gave the target compound in near quantitative yield. UV-Vis (CH$_2$Cl$_2$) 375 nm, 411 nm, 500 nm, 533 nm, 678 nm, 738 nm, 785 nm, 894 nm. FTIR (KBr) 1500 cm$^{-1}$, 1463 cm$^{-1}$, 1384 cm$^{-1}$, 1321 cm$^{-1}$, 1263 cm$^{-1}$, 1208 cm$^{-1}$, 1182 cm$^{-1}$, 1162 cm$^{-1}$, 1129 cm$^{-1}$, 1109 cm$^{-1}$, 1065 cm$^{-1}$, 1001 cm$^{-1}$. MALDI-TOF MS: calcd. for C$_{90}$H$_{72}$Cl$_2$Fe$_2$N$_8$ 1446.396 m/z, obsd. 1446.700 m/z.

Characterization

Figure 3A:
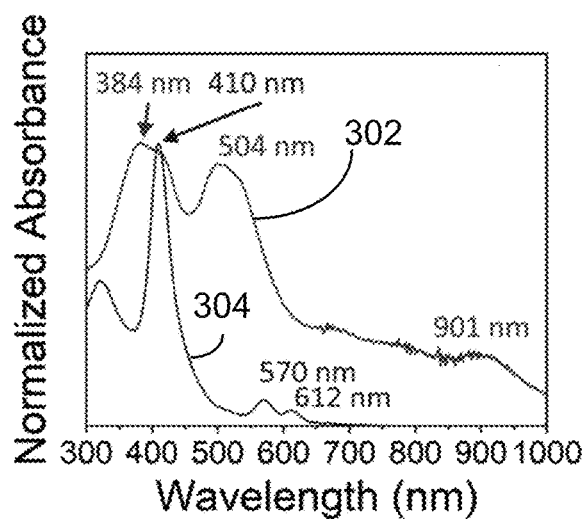
FIG. 3A shows normalized absorption spectra of $[Fe_2FP]Cl_2$ and [FeTTP]Cl.
Figure 3B:
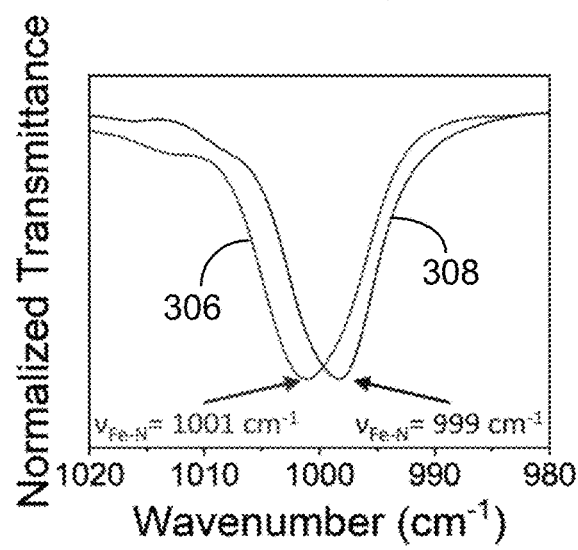
FIG. 3B shows normalized Fourier transform infrared (FTIR) transmission spectra of $[Fe_2FP]Cl_2$ and [FeTTP]Cl.
Figure 3C:
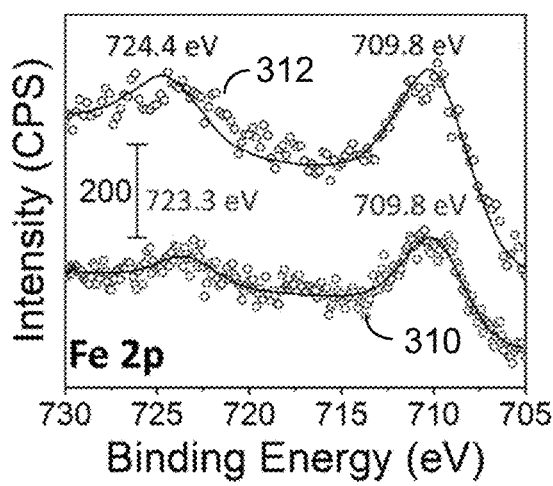
FIG. 3C shows high energy resolution core level XP spectra recorded using samples of $[Fe_2FP]Cl_2$ or [FeTTP]Cl.
Figure 3D:
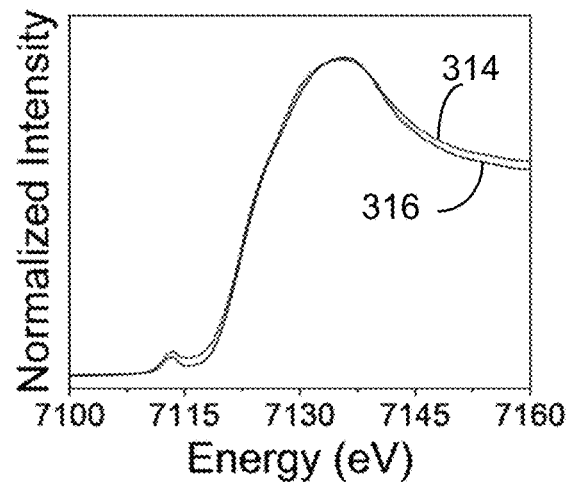
FIG. 3D shows X-ray absorption near-edge spectroscopy (XANES) spectra of $[Fe_2FP]Cl_2$ and [FeTTP]Cl.

FIG. 3A shows a normalized absorption spectra of [Fe$_2$FP]Cl$_2$ 302 and [FeTTP]Cl 304 recorded in DMF. FIG. 3B shows normalized Fourier transform infrared (FTIR) transmission spectra of [Fe$_2$FP]Cl$_2$ 306 and [FeTTP]Cl 308 recorded in pressed KBr pellets. FIG. 3C shows high energy resolution core level XP spectra of the Fe 2p region recorded using samples of [Fe$_2$FP]Cl$_2$ 310 or [FeTTP]Cl 312 dropcasted onto a glassy carbon disk. The solid lines are the component fits. FIG. 3D shows X-ray absorption near-edge spectroscopy (XANES) spectra at the Fe K-edge of [Fe$_2$FP]Cl$_2$ 314 and [FeTTP]Cl 316.

Successful metal insertion was confirmed using MALDI-TOF spectrometry, as well as UV-Vis (FIG. 3A) and FTIR spectroscopies (FIG. 3B). In addition, both X-ray photoelectron spectroscopy (XPS) (FIG. 3C) and X-ray absorption near-edge spectroscopy (XANES) (FIG. 3D) indicate a +3 oxidation state of the Fe centers in both [Fe$_2$FP]Cl$_2$ and [FeTTP]Cl.

Unlike the electronic absorption spectrum of [FeTTP]Cl shown in FIG. 3A and recorded in dimethylformamide (DMF), which displays a single Soret-band transition centered at 410 nm and two Q-band transitions centered at 570 nm and 612 nm, the spectrum of [Fe$_2$FP]Cl$_2$ in DMF displays two Soret-like absorption bands centered at 384 nm and 504 nm, as well as a Q-type absorption feature at 901 nm (FIG. 3A). The relatively red absorption features associated with [Fe$_2$FP]Cl$_2$ versus [FeTTP]Cl are consistent with the extended aromaticity of the fused architecture (i.e., a 36 π-aromatic ligand versus an 18 π-aromatic ligand). The wavelengths of the Soret and Q-type absorption bands from absorption spectra recorded in dichloromethane (CH$_2$Cl$_2$), benzonitrile (C$_6$H$_5$CN), and butyronitrile (C$_3$H$_7$CN) are provided in Tables 1 and 2.

TABLE 1

Wavelengths of Soret-like and Q-like absorption bands of [Fe$_2$FP]Cl$_2$ in different solvents.

| | Soret-absorption band(s) (nm) | Q-absorption band(s) (nm) |
|---|---|---|
| C$_3$H$_7$CN | 373, 409,$^a$ 496, 524 | 670, 737, 794, 879 |
| CH$_2$Cl$_2$ | 375, 411,$^a$ 500, 533 | 678, 738, 785, 894 |
| DMF | 384, 518 | 901 |
| C$_6$H$_5$CN | 380, 413, 502, 534 | 683, 746, 793, 892 |

$^a$This absorption feature appears as a shoulder

TABLE 2

Wavelengths of Soret-and Q-absorption bands of [FeTTP]Cl in different solvents.

| | Soret-absorption band(s) (nm) | Q-absorption band(s) (nm) |
|---|---|---|
| C$_3$H$_7$CN | 378, 417 | 509, 571, 658,$^a$ 688 |
| CH$_2$Cl$_2$ | 381, 418 | 511, 574.5, 663,$^a$ 692 |
| DMF | 322, 410 | 570, 612 |
| C$_6$H$_5$CN | 351,$^a$ 421 | 509, 572, 641, 684 |

$^a$This absorption feature appears as a shoulder

FTIR data collected using a matrix of KBr containing either [FeTTP]Cl or [Fe$_2$FP]Cl$_2$ show distinct transmission bands centered at 999 cm$^{-1}$ and 1001 cm$^{-1}$, respectively (FIG. 3B). These bands are assigned to an in-plane porphyrin deformation vibration ($v_{Fe-N}$, where v is the vibrational frequency). In general, this vibrational mode is sensitive to both the elemental nature of the porphyrin metal center and its local coordination environment. For these reasons, in-plane porphyrin deformation vibrations have been used as diagnostic signals for indicating the presence of metalloporphyrins on surfaces and gaining information on their local chemical environments. The difference in $v_{Fe-N}$ frequencies of [FeTTP]Cl and [Fe$_2$FP]Cl$_2$ suggests the fused complex provides a more rigid ligand motif.

High resolution Fe core level XP spectra collected using either samples of the fused or monomeric complexes display peaks centered at 709.8 eV (2p$_{3/2}$) and 723.3 eV (2p$_{1/2}$) in the case of [Fe$_2$FP]Cl$_2$, and peaks centered at 709.8 eV (2p$_{3/2}$) and 724.4 eV (2p$_{1/2}$) in the case of [FeTTP]Cl (FIG. 3C). These results are consistent with Fe(III) oxidation states for the metal centers of these overall charge neutral complexes, where [Fe$_2$FP]Cl$_2$ features two anionic (X-type) chloride ligands, four anionic (X-type) nitrogen ligand sites, and four charge-neutral (L-type) nitrogen ligand sites, whereas [FeTTP]Cl features one anionic (X-type) chloride ligand, two anionic (X-type) nitrogen ligand sites, and two charge-neutral (L-type) nitrogen ligand sites. In addition, XANES indicates similar edge energies for the fused and non-fused complexes (FIG. 3D), with values that are intermediate to those recorded using FeCl$_2$ (Fe$^{II}$) and Fe$_2$O$_3$ (Fe$^{III}$) as reference compounds.

In this disclosure, the redox states of the binuclear iron-fused porphyrin and the structurally related mononuclear complex are described using the monikers [Fe$_2$FP]$^n$ and [FeTTP]$^n$ respectively, where n gives information on the relative number of electrons transferred to or from the charge neutral [Fe$_2$FP]$^0$ or [FeTTP]$^0$ metalloporphyrin complexes. Electrochemical potentials associated with the interconversion between the [Fe$_2$FP]$^{2+}$ through [Fe$_2$FP]$^{4-}$ redox states were determined using both cyclic voltammetry and differential pulse voltammetry. Related measurements using [FeTTP]Cl and involving the interconversion between the [FeTTP]$^{1+}$ through [FeTTP]$^{2-}$ redox states, are included for comparison.

Figure 4A:
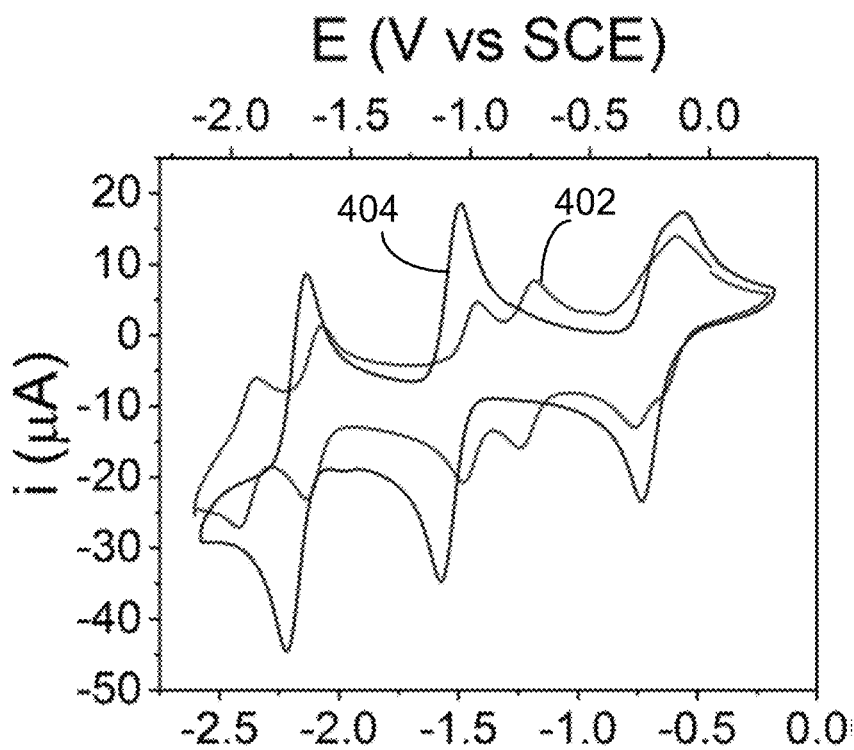
FIG. 4A shows cyclic voltammograms of $[Fe_2FP]Cl_2$ and [FeTTP]Cl.
Figure 4B:
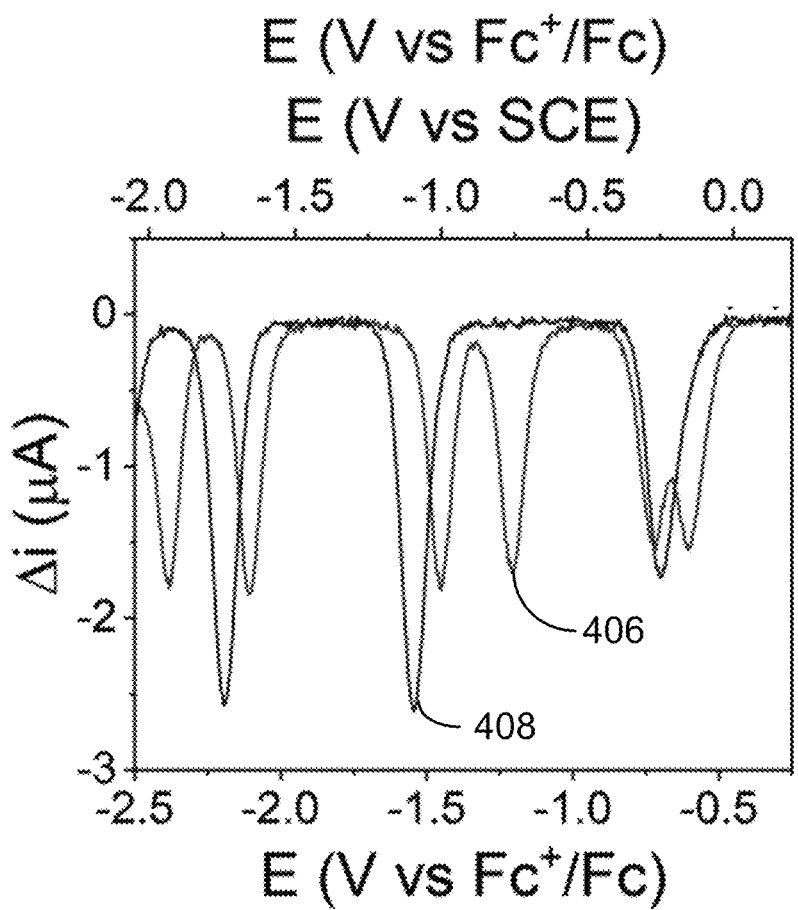
FIG. 4B shows differential pulse voltammetry data of $[Fe_2FP]Cl_2$ and [FeTTP]Cl.

FIG. 4A shows cyclic voltammograms of 1.0 mM [Fe$_2$FP]Cl$_2$ 402 and [FeTTP]Cl 404 recorded in a 0.1 M tetrabutylammonium hexafluorophosphate TBAPF$_6$ DMF solution under argon at a scan rate of 250 mV s$^{-1}$. FIG. 4B shows differential pulse voltammetry data of 1.0 mM [Fe$_2$FP]Cl$_2$ 406 and [FeTTP]Cl 408 solutions recorded with a pulse height of 2.5 mV, a pulse width of 100 ms, a step height of −5 mV, and a step time of 500 ms. All measurements were recorded using a 3 mm diameter glassy carbon working electrode at room temperature and the ferrocenium/ferrocene redox couple as an internal reference.

Voltammograms recorded using [Fe$_2$FP]Cl$_2$ (1.0 mM) dissolved in 0.1 M TBAPF$_6$ in DMF indicate a pair of overlapping redox features appearing between the range of −0.50 V and −0.80 V versus the ferrocenium/ferrocene (V vs Fc$^+$/Fc) redox couple. These features are assigned to a pair of chemically and electrochemically irreversible couples, where the chemical irreversibility is likely due to loss of X-type chloride ligands following reduction of the porphyrin complexes. In addition, two pairs of quasi-reversible redox couples are observed at more negative potentials with midpoint potentials equal to −1.21, −1.46, −2.11, and −2.40 V vs Fc$^+$/Fc, respectively (where $^nE_{1/2}$ is estimated as the average of anodic and cathodic peak potentials for a given quasi-reversible redox couple and $^{III}E_{1/2}$, $^{IV}E_{1/2}$ $^VE_{1/2}$, and $^{VI}E_{1/2}$ are reported as reduction half reactions by convention) (FIG. 4A).

For comparison, when measured under otherwise similar experimental conditions, cyclic voltammograms recorded using [FeTTP]Cl display one non-reversible redox feature appearing between the range of −0.50 and −0.80 V vs Fc$^+$/Fc, as well as two quasi-reversible redox couples with midpoint potentials ($^{II}E_{1/2}$ and $^{III}E_{1/2}$) equal to −1.53 V vs Fc$^+$/Fc and −2.18 V vs Fc$^+$/Fc respectively (FIG. 4A).

The midpoint potentials, and peak potentials in the case of non-reversible redox features, recorded using [Fe$_2$FP]Cl$_2$ or [FeTTP]Cl in DMF are summarized in Tables 3 and 4. Referring to Table 3, midpoint potentials ($^nE_{1/2}$) of [Fe$_2$FP]Cl$_2$ were determined by cyclic voltammetry and reported as reduction half-reaction by convention. Peak-to-peak separations ($\Delta E_p$) are reported in parentheses. All voltammograms were collected under argon and at room temperature using a 3 mm diameter glassy carbon working electrode immersed in solutions containing 1 mM porphyrin and 0.1 M TBAPF$_6$ in butyronitrile, dichloromethane, dimethylformamide, or benzonitrile. In all of these experiments, the ferrocenium/ferrocene redox couple was used as an internal reference. Referring to Table 4, midpoint potentials ($^nE_{1/2}$) of [FeTTP]Cl were determined by cyclic voltammetry and reported as reduction half-reactions by convention. Peak-to-peak separations ($\Delta E_p$) are reported in parentheses. All voltammograms were collected under argon and at room temperature using a 3 mm diameter glassy carbon working electrode immersed in solutions containing 1 mM porphyrin and 0.1 M TBAPF$_6$ in butyronitrile, dichloromethane, dimethylformamide, or benzonitrile. In all of these experiments, the ferrocenium/ferrocene redox couple was used as an internal reference Referring to Table 5, cathodic peak potentials of [Fe$_2$FP]Cl$_2$ and [FeTTP]Cl were determined by differential pulse voltammetry. An assignment of the related redox couple is indicated in parenthesis. All voltammograms were collected under argon and at room temperature using a 3 mm diameter glassy carbon working electrode immersed in solutions containing 1 mM porphyrin and 0.1 M TBAPF$_6$ in dimethylformamide. In all of these experiments, the ferrocenium/ferrocene cathodic peak potential was used as an internal reference. Table 5 includes cathodic peak potentials measured in FIG. 4B, which enables resolution of the overlapping redox waves associated with the conversion of [Fe$_2$FP]$^{2+}$ to [Fe$_2$FP]$^{1+}$ and [Fe$_2$FP]$^{1+}$ to [Fe$_2$FP]$^0$. The height of the peaks corresponding to reductions from [Fe$_2$FP]$^0$ to [Fe$_2$FP]$^{4-}$ are approximately equal in value (FIG. 4B), consistent with each reduction processes being attributed to one-electron chemistry. The slightly lower peak height (~90% lower) for the peaks corresponding to reductions from [Fe$_2$FP]$^{2+}$ to [Fe$_2$FP]$^0$ are attributed to sluggish heterogeneous electron-transfer kinetics (electrochemical irreversibility) and/or dissociation of Cl$^-$ ligands following the reduction of iron centers (chemical irreversibility), both of which could result in a larger peak width and lower peak intensity. Information on the midpoint and peak potentials of cyclic voltammograms recorded in other solvents, including CH$_2$Cl$_2$, C$_6$H$_5$CN, and C$_3$H$_7$CN, are provided in Tables 3 and 4.

TABLE 3

Midpoint potentials ($^nE_{1/2}$) of [Fe$_2$FP]Cl$_2$ as determined by cyclic voltammetry $^nE$ (V vs Fc$^+$/Fc)

| [Fe$_2$FP]Cl$_2$ | $^{VI}E$ ($\Delta E_p$, mV) [Fe$_2$FP]$^{3-}$/[Fe$_2$FP]$^{4-}$ | $^VE$ ($\Delta E_p$, mV) [Fe$_2$FP]$^{2-}$/[Fe$_2$FP]$^{3-}$ | $^{IV}E$ ($\Delta E_p$, mV) [Fe$_2$FP]$^{1-}$/[Fe$_2$FP]$^{2-}$ | $^{III}E$ ($\Delta E_p$, mV) [Fe$_2$FP]$^0$/[Fe$_2$FP]$^{1-}$ | $^{II}E$ ($\Delta E_p$, mV) [Fe$_2$FP]$^{1+}$/[Fe$_2$FP]$^0$ | $^IE$ ($\Delta E_p$, mV) [Fe$_2$FP]$^{2+}$/[Fe$_2$FP]$^{1+}$ |
|---|---|---|---|---|---|---|
| C$_3$H$_7$CN | — | −2.16$^a$ (89) | −1.48$^a$ (69) | −1.21$^a$ (69) | −0.84$^a$ (69) | −0.67$^a$ (55) |
| CH$_2$Cl$_2$ | — | — | −1.55$^a$ (102) | −1.18$^a$ (102) | −0.69$^b$/−0.89$^c$ | — |
| DMF | −2.40$^a$ (81) | −2.11$^a$ (75) | −1.46$^a$ (74) | −1.21$^a$ (75) | −0.71$^b$/−0.76$^c$ | −0.56$^b$/−0.64$^c$ |
| C$_6$H$_6$CN | — | — | −1.49$^b$/−1.58$^c$ | −1.35$^b$/−1.48$^c$ | −0.42$^b$/−0.87$^c$ | −0.26$^b$/−0.72$^c$ |

$^aE = E_{1/2}$; electrochemically reversible or quasi-reversible
$^bE$ = anodic peak potential; electrochemically irreversible
$^cE$ = cathodic peak potential; electrochemically irreversible

TABLE 4

Midpoint potentials ($^nE_{1/2}$) of [FeTTP]Cl as determined by cyclic voltammetry $^nE$ (V vs Fc$^+$/Fc)

| [FeTTP]Cl | $^{III}E$ ($\Delta E_p$, mV) [FeTTP]$^{1-}$/[FeTTP]$^{2-}$ | $^{II}E$ ($\Delta E_p$, mV) [FeTTP]$^0$/[FeTTP]$^{1-}$ | $^IE$ ($\Delta E_p$, mV) [FeTTP]$^{1+}$/[FeTTP]$^0$ |
|---|---|---|---|
| C$_3$H$_7$CN | −2.21$^a$ (89) | −1.54$^a$ (89) | −0.78$^a$ (92) |
| CH$_2$Cl$_2$ | — | −1.57$^a$ (140) | −0.71$^b$/−0.86$^c$ |
| DMF | −2.18$^a$ (87) | −1.53$^a$ (80) | −0.56$^b$/−0.73$^c$ |
| C$_6$H$_5$CN | — | −1.60$^a$ (110) | −0.40$^b$, −0.72$^b$/−0.84$^c$ |

$^aE = E_{1/2}$; electrochemically reversible or quasi-reversible
$^bE$ = anodic peak potential; electrochemically irreversible
$^cE$ = cathodic peak potential; electrochemically irreversible

TABLE 5

Cathodic peak potentials of [Fe$_2$FP]Cl$_2$ and [FeTTP]Cl as determined by differential pulse voltammetry.

$^nE$ (V vs Fc$^+$/Fc)

| | $^{VI}E$ | $^VE$ | $^{IV}E$ | $^{III}E$ | $^{II}E$ | $^IE$ |
|---|---|---|---|---|---|---|
| [Fe$_2$FP]Cl$_2$ | −2.38 [Fe$_2$FP]$^{3-}$/[Fe$_2$FP]$^{4-}$ | −2.11 [Fe$_2$FP]$^{2-}$/[Fe$_2$FP]$^{3-}$ | −1.45 [Fe$_2$FP]$^{1-}$/[Fe$_2$FP]$^{2-}$ | −1.20 [Fe$_2$FP]$^0$/[Fe$_2$FP]$^{1-}$ | −0.71 [Fe$_2$FP]$^{1+}$/[Fe$_2$FP]$^0$ | −0.60 [Fe$_2$FP]$^{2+}$/[Fe$_2$FP]$^{1+}$ |
| [FeTTP]Cl | | | | −2.20 [FeTTP]$^{1-}$/[FeTTP]$^{2-}$ | −1.54 [FeTTP]$^0$/[FeTTP]$^{1-}$ | −0.70 [FeTTP]$^{1+}$/[FeTTP]$^0$ |

UV-Vis-near infrared spectroelectrochemistry (UV-Vis-NIR-SEC) and infrared spectroelectrochemistry (IR-SEC) allow comparisons of changes in electronic and vibrational structure following reduction of the fused porphyrin macrocycles and their model monomeric analogs.

FIGS. 5A-5C show UV-Vis-NIR absorption spectra of [Fe$_2$FP]Cl$_2$ (0.05 mM) recorded in a 0.1 M TBAPF$_6$ DMF solution polarized at potentials to generate [Fe$_2$FP]$^{2+}$ 502, [Fe$_2$FP]$^0$ 504, [Fe$_2$FP]$^{1-}$ 506, [Fe$_2$FP]$^{2-}$ 508, [Fe$_2$FP]$^{3-}$ 510, and [Fe$_2$FP]$^{4-}$ 512. FIGS. 5D-5F show spectra of [FeTTP]Cl (0.05 mM) recorded in a 0.1 M TBAPF$_6$ DMF solution polarized at potentials to generate [FeTTP]$^{1+}$ 514, [FeTTP]$^0$ 516, [FeTTP]$^{1-}$ 518, and [FeTTP]$^{2-}$ 520.

Referring to FIG. 5A, UV-Vis-NIR-SEC measurements recorded using [Fe$_2$FP]Cl$_2$ in DMF (0.05 mM) indicate the two-electron reduction of [Fe$_2$FP]$^{2+}$ 502 to form [Fe$_2$FP]$^0$ 504 gives rise to a bathochromically-shifted, Soret-like absorption band centered at 430 nm as well as two other secondary Soret-like bands centered at 499 nm and 545 nm, and a hypsochromically-shifted Q-like band centered at 809 nm. Under the conditions used in this analysis, a spectrum associated with the one-electron reduction of [Fe$_2$FP]$^{2+}$ to form [Fe$_2$FP]$^{1+}$ was not resolved. Polarizing the working electrode to more negative potentials gives rise to further spectroscopic transitions that are assigned to reduction of [Fe$_2$FP]$^0$ 504 to form [Fe$_2$FP]$^{1-}$ 506 (FIG. 5B), whereupon the Soret-like band at 430 nm decreases in intensity, the secondary Soret-like bands at 499 nm and 545 nm are replaced by a broad absorption feature, and the Q-like band centered at 809 nm is replaced by a Q-like band center at ~880 nm. Further reduction to form [Fe$_2$FP]$^{2-}$ 508 results in the appearance of a bathochromically-shifted, Soret-like band at 439 nm, the growth of a new secondary Soret-like band at 594 nm, and an increase in the intensity of the Q-like band centered at ~880 nm (FIG. 5B). The reduction of [Fe$_2$FP]$^{2-}$ 508 to form [Fe$_2$FP]$^{3-}$ 510 shows a loss of the secondary Soret-like band at 594 nm, the rise of a new secondary Soret-like band at 562 nm, and a decrease in the intensity of the Q-like band at ~880 nm (FIG. 5C). Finally, the conversion of [Fe$_2$FP]$^{3-}$ 510 to [Fe$_2$FP]$^{4-}$ 512 is associated with a loss of the secondary Soret-like absorption at 562 nm, and an increase in the intensity of the Soret-like band at 438 nm (FIG. 5C). The presence of well-defined isosbestic points at 369 nm, 447 nm, 474 nm, and 577 nm during the conversion of [Fe$_2$FP]$^0$ 504 to [Fe$_2$FP]$^{1-}$ 506, 400 nm and 567 nm for the conversion of [Fe$_2$FP]$^{1-}$ 506 to [Fe$_2$FP]$^{2-}$ 508, 575 nm, 658 nm, and 774 nm for the conversion of [Fe$_2$FP]$^{2-}$ 508 to [Fe$_2$FP]$^{3-}$ 510, as well as at 524 nm and 641 nm for the conversion of [Fe$_2$FP]$^{3-}$ 501 to [Fe$_2$FP]$^{4-}$ 512, are consistent with relatively stable conversion from one redox state to the next without the formation of intermediates or decomposition products.

FIGS. 5D-5F show spectra of [FeTTP]Cl (0.05 mM) recorded in a 0.1 M TBAPF$_6$ DMF solution polarized at potentials to generate [FeTTP]$^{1+}$ 514, [FeTTP]$^0$ 516, [FeTTP]$^{1-}$ 518, and [FeTTP]$^{2-}$ 520 UV-Vis-NIR-SEC data collected using [FeTTP]Cl in DMF (0.05 mM) show the one-electron reduction of [FeTTP]$^{1+}$ 514 to form [FeTTP]$^0$ 516 results in a loss of the Soret-band and the rise of a bathochromically-shifted Soret-band centered at 433 nm (FIG. 5D). Further reduction from [FeTTP]$^0$ 516 to form [FeTTP]$^{1-}$ 518 results in in a decreased intensity of the Soret-band at 433 nm and the appearance of new bands at 428 nm and 394 nm (FIG. 5E). Finally, the conversion of [FeTTP]$^{1-}$ 518 to [FeTTP]$^{2-}$ 520 results in the loss of the bands at 394 nm and 428 nm, and the rise of two new absorption bands at 365 nm and 436 nm (FIG. 5F). These tests were performed over the same range of potentials that were used to collect the UV-Vis-NIR-SEC data for [Fe$_2$FP] Cl$_2$ and show relatively clean spectroscopic transitions associated with the [FeTTP]$^{2+}$/[FeTTP]$^{1+}$, [FeTTP]$^{1+}$/[FeTTP]$^0$, and [FeTTP]$^0$/[FeTTP]$^{1-}$ redox couples. The presence of well-defined isosbestic points at 418 nm and 450 nm during the conversion of [FeTTP]$^{1+}$ 514 to [FeTTP]$^0$ 516, 421 nm and 445 nm during the conversion of [FeTTP]$^0$ 516 to [FeTTP]$^{1-}$ 518, as well as at 380 nm during the conversion of [FeTTP]$^{1-}$ 518 to form [FeTTP]$^{2-}$ 520, are consistent with stable conversion from one redox state to the next without the formation of intermediates or decomposition products. To better observe the spectroscopic changes in the Q-band region, experiments were also recorded using higher concentrations of [FeTTP]Cl (0.25 mM).

FIGS. 6A-6C show FTIR absorption spectra of [Fe$_2$FP] Cl$_2$ (1.0 mM) recorded in a 0.1 M TBAPF$_6$ DMF solution polarized at potentials to generate [Fe$_2$FP]$^{2+}$ 602, [Fe$_2$FP]$^0$ 604, [Fe$_2$FP]$^{1-}$ 606, [Fe$_2$FP]$^{2-}$ 608, and [Fe$_2$FP]$^{3-}$ 610.

IR-SEC measurements recorded using [Fe$_2$FP]Cl$_2$ or [FeTTP]Cl in DMF (1.0 mM or 0.4 mM, respectively) show that upon reduction of these complexes there are distinct changes in the frequency range characteristic of in-plane iron porphyrin deformation vibrations. The two-electron reduction of [Fe$_2$FP]$^{2+}$ 602 to form [Fe$_2$FP]$^0$ 604 gives rise to a relatively broad band centered at 1000 cm$^{-1}$ (FIG. 6A). As in the case of the UV-Vis-NIR-SEC tests, a spectrum for the one-electron reduction from [Fe$_2$FP]$^{2+}$ to [Fe$_2$FP]$^{1+}$ was not resolved under the conditions used in these IR-SEC experiments. Further reduction, to form [Fe$_2$FP]$^{1-}$ 606, gives rise to new bands centered at 1007 cm$^{-1}$ and 993 cm$^{-1}$, and the reduction of [Fe$_2$FP]$^{1-}$ 606 to form [Fe$_2$FP]$^{2-}$ 608 results in a loss of the band at 993 cm$^{-1}$ and an increase in the band at 1007 cm$^{-1}$ (FIG. 6B). Finally, the reduction of [Fe$_2$FP]$^{2-}$ 608 to form [Fe$_2$FP]$^{3-}$ 610 shows a decrease in the intensity of the band centered at 1007 cm$^{-1}$, along with an increase of a broad band centered at 993 cm$^{-1}$ (FIG. 6C). Further reduction, to obtain spectra associated with formation of [Fe$_2$FP]$^{4-}$, was not detected using the IR-SEC cell configuration for this analysis.

FIGS. 6D-6E show spectra of [FeTTP]Cl (0.4 mM) recorded in a 0.1 M TBAPF$_6$ DMF solution polarized at potentials to generate [FeTTP]$^{1+}$ 612, [FeTTP]$^0$ 614, and [FeTTP]$^{1-}$ 616. In the case of IR-SEC measurements recorded using [FeTTP]Cl, one-electron reduction to form [FeTTP]$^0$ 614 results in a shift of $\nu_{Fe-N}$ from 999 cm$^{-1}$ to 991 cm$^{-1}$ ($\Delta\nu_1$=8 cm$^{-1}$) (FIG. 6D), while further reduction from [FeTTP]$^0$ 614 to [FeTTP]$^{1-}$ 616 yields further displacement from 991 cm$^{-1}$ to 985 cm$^{-1}$ ($\Delta\nu_2$=6 cm$^{-1}$) (FIG. 6E). Further reduction, to obtain spectra associated with formation of [FeTTP]$^{2-}$, was not detected using the cell configuration for this analysis.

Materials

All compounds were synthesized from commercially available starting materials. All reagents were purchased from commercial suppliers and used as received without further purification. Solvents were obtained from Fisher Scientific (dichloromethane, hexanes, toluene, and methanol) or Sigma-Aldrich (butyronitrile, dimethylformamide, and benzonitrile), and were distilled before use.

Instrumentation

Mass Spectra. Mass spectra of all compounds were obtained with Voyager DE STR matrix-assisted laser desorption/ionization time-of-flight (MALDI-TOF) mass spectrometer in positive ion using trans, trans-1,4-diphenyl-1,3-butadiene as a matrix.

Nuclear Magnetic Resonance. $^1$H-NMR spectra were recorded on a Varian MR400 spectrometer operating at 400 MHz, in deuterated chloroform (CDCl$_3$). Chemical shifts ($\delta$) are reported in parts per million (ppm) relative to residual trimethylsilane (TMS) peak.

Electrochemistry. All voltammetry measurements were performed with a Biologic SP-300 potentiostat using a glassy carbon (3 mm diameter) working electrode, a platinum counter electrode, and a silver wire pseudoreference electrode in a conventional three-electrode cell at 250 mV s$^{-1}$ scan rate. All measurements were made at room temperature under argon. The potential of the silver wire pseudoreference electrode was determined using the ferrocenium/ferrocene redox couple as an internal standard and adjusting to V vs SCE (standard calomel electrode). Benzonitrile, butyronitrile, dichloromethane, or dimethylformamide were used as solvents. Electrochemical analysis grade tetrabutylammonium hexafluorophosphate (TBAPF$_6$) electrolyte was obtained from Aldrich and stored in a desiccator containing calcium sulfate (CaSO$_4$) as a desiccant. The supporting electrolyte concentration of all electrochemical measurements was 0.1 M TBAPF$_6$, and the working electrode was cleaned between experiments by polishing with alumina (50 nm diameter) slurry, followed by solvent rinses.

UV-Vis-NIR and UV-Vis-NIR-SEC. All ultraviolet-visible-near-infrared (UV-Vis-NIR) spectra were recorded on a Shimadzu SolidSpec-3700 spectrometer with a deuterium (D2) lamp for the ultraviolet range and a WI (halogen) lamp for the visible and near-infrared, using benzonitrile, butyronitrile, dichloromethane, or dimethylformamide as solvents. Ultraviolet-visible-near-infrared spectroelectrochemistry (UV-Vis-NIR-SEC) measurements were recorded using a Biologic SP-200 potentiostat, a Pt honeycomb design working electrode, a Pt counter electrode, and a silver wire pseudoreference electrode. In all experiments, the supporting electrolyte contained 0.1 M TBAPF$_6$ and was sparged with argon. Thin layer constant potential electrolysis was monitored via UV-Vis-NIR as the working electrode was polarized in a stepwise manner (i.e., an incrementally increasing bias potential versus the silver wire reference). Before changing the electrode polarization, absorption spectra were continuously collected at each applied potential until there were no significant changes in the resulting absorption spectra. This procedure was repeated until increasing the polarization no longer resulted in significant changes between UV-Vis-NIR spectra collected prior to and following the potential step. The Pt honeycomb electrode was cleaned between experiments by collecting cyclic voltammograms in 0.1 M H$_2$SO$_4$, followed by rinsing with 18.2 MΩ cm water and then acetone. The potential of the pseudoreference electrode was determined by measuring the ferrocenium/ferrocene redox couple under identical solvent conditions before and after completion of the measurements.

FTIR and IR-SEC. Fourier transform infrared (FTIR) spectra were recorded on a Bruker Vertex 70, in pressed KBr pellets using a transmission mode at 64 scans with a 1 cm$^{-1}$ resolution, GloBar MIR source, a broadband KBr beamsplitter, and a liquid nitrogen cooled MCT detector. Background measurements were obtained from the air, and baselines were corrected for rubberband scattering. The data were processed using OPUS software. Infrared spectroelectrochemistry (IR-SEC) measurements were performed using a Biologic potentiostat connected to a custom optically transparent thin-layer electrochemical cell (path length: 0.2 mm) equipped with NaCl optical windows and purchased from Professor Frantisek Hard, University of Reading. The cell contained a Pt mesh counter electrode, a silver wire pseudoreference electrode, and a Pt mesh working electrode. In all experiments the supporting electrolyte contained 0.1 M TBAPF$_6$ and was sparged with argon. The Pt mesh working electrode was positioned within the light path of the IR spectrophotometer. The cell and its contents were sealed under an argon atmosphere prior to all measurements, and thin layer constant potential electrolysis was monitored via FTIR as the working electrode was polarized in a stepwise manner (i.e., an incrementally increasing bias potential versus the silver wire reference). Before changing the electrode polarization, absorption spectra were continuously collected at each applied potential until there were no significant changes in the resulting absorption spectra. This procedure was repeated until increasing the polarization no longer resulted in significant changes between FTIR spectra collected prior to and following the potential step. The cell was disassembled and cleaned between experiments by rinsing the cell components first with water, followed by acetone, and finally dichloromethane. A drop of nitric acid was placed on the Pt mesh working electrode for approximately 5-10 min before rinsing with water.

XPS. X-ray Photoelectron Spectroscopy was performed using a monochromatized Al Kα source (hv=1486.6 eV), operated at 63 W, on a VG ESCALAB 220i-XL (Thermo Fisher) system at a takeoff angle of 0° relative to the surface normal and a pass energy for narrow scan spectra of 20 eV at an instrument resolution of ~700 meV. Survey spectra were collected with a pass energy of 150 eV. Spectral analysis was performed using Casa XPS analysis software, and all spectra were calibrated by adjusting C is core level position to 284.8 eV.

X-ray Absorption Near Edge Structure (XANES). XANES analyses were conducted at the SAMBA beamline, Synchrotron SOLEIL, France. The electron storage ring was operated at 2.75 GeV. A Si(220) double crystal monochromator was used, which was calibrated by assigning the first inflection of a Fe foil XANES spectrum to 7111.2 eV. The XANES spectra were collected in transmission mode using an N$_2$-filled ionization chamber. Spectra were collected from 6900 to 8000 eV using a continuous scan acquisition mode, with a 5 eV s$^{-1}$ velocity and 0.04 s point$^{-1}$ integration time. Each scan was obtained in 220 seconds and featured 5500 data points with a 0.2 eV step size. Multiple spectra were repeatedly collected for each sample until their average spectrum had a satisfying signal-to-noise ratio. All XAS data processing was done using the Athena program of the Demeter software suite.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A binuclear iron-fused porphyrin having the structure:

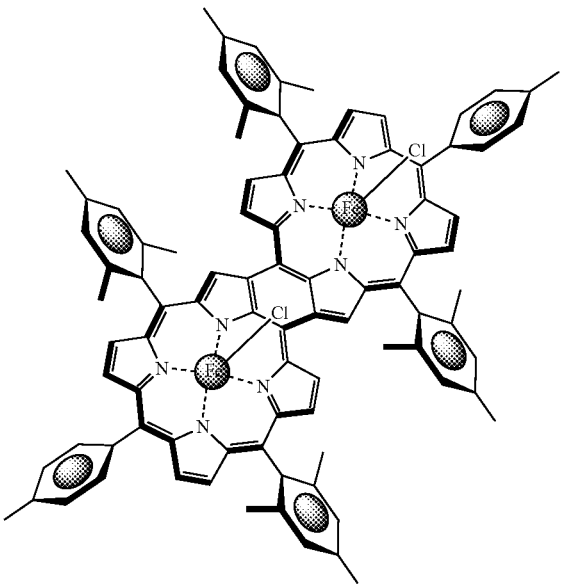

2. A method of synthesizing a binuclear fused porphyrin, the method comprising:
   combining free-base fused-porphyrin and a solvent to yield a solution;
   refluxing the solution;
   combining a metal salt with the solution; and
   removing the solvent from the solution to yield the binuclear fused porphyrin, wherein the binuclear fused porphyrin is represented by the following structure:

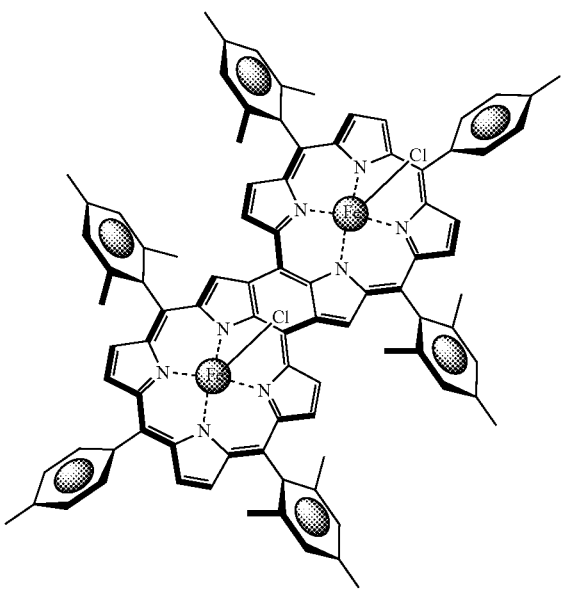

3. The method of claim 2, wherein the solvent comprises dichloromethane and methanol.

4. The method of claim 3, wherein a volume ratio of dichloromethane to methanol is about 5:1.

5. The method of claim 2, wherein the metal salt comprises $FeCl_2$.

6. The method of claim 2, wherein a molar ratio of the metal salt to the free-base fused-porphyrin is about 60:1.

7. The method of claim 2, wherein refluxing the solution occurs under an argon atmosphere.

8. The method of claim 2, wherein removing the solvent occurs at a pressure below one atmosphere.

9. The method of claim 2, wherein combining the metal salt with the solution comprises combining the metal salt in discrete portions over time.

10. The method of claim 2, further comprising purifying the binuclear fused porphyrin.

\* \* \* \* \*